United States Patent
Hirakawa et al.

(10) Patent No.: US 11,093,699 B2
(45) Date of Patent: Aug. 17, 2021

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventors: Shinnosuke Hirakawa, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/289,129

(22) Filed: Feb. 28, 2019

(65) Prior Publication Data

US 2019/0279408 A1 Sep. 12, 2019

(30) Foreign Application Priority Data

Mar. 6, 2018 (JP) .............................. JP2018-040202

(51) Int. Cl.
*G06T 11/60* (2006.01)
*G06F 40/169* (2020.01)

(52) U.S. Cl.
CPC ............ *G06F 40/169* (2020.01); *G06T 11/60* (2013.01); *G06T 2210/41* (2013.01)

(58) Field of Classification Search
CPC ...... G06T 11/60; G06T 2210/41; G06F 40/20
See application file for complete search history.

(56) References Cited

U.S. PATENT DOCUMENTS 6,820,237 B1 * 11/2004 Abu-Hakima ........ G06F 40/117
715/210
9,449,080 B1 * 9/2016 Zhang ................. G06F 16/3331
10,198,436 B1 * 2/2019 Dockhorn ............... G06F 40/47
2005/0049495 A1 * 3/2005 Sumanaweera .......... A61B 8/00
600/437
2007/0237377 A1 * 10/2007 Oosawa ............... G06K 9/3233
382/128
2009/0076853 A1 3/2009 Sagawa
2012/0183188 A1 7/2012 Moriya
(Continued)

FOREIGN PATENT DOCUMENTS

JP 2003/260030 A 9/2003
JP 2005-160502 * 6/2005 .............. A61B 5/00
JP 2009-045131 A 3/2009
(Continued)

OTHER PUBLICATIONS

Japanese Office Action dated Mar. 30, 2021 in Japanese Patent Application No. 2018-040202, with English translation.

*Primary Examiner* — Ryan R Yang
(74) *Attorney, Agent, or Firm* — Birch, Stewart, Kolasch & Birch, LLP

(57) ABSTRACT

An image receiving unit receives a current image acquired by imaging a subject. A character information acquisition unit acquires character information from past medical information relevant to the current image. A position receiving unit receives a designation of a position in the current image. A character specifying unit specifies characters relevant to the position received by the position receiving unit from the character information acquired by the character information acquisition unit. A display control unit performs control to display the character specified by the character specifying unit so as to be emphasized on a display unit.

10 Claims, 14 Drawing Sheets

(56) References Cited

U.S. PATENT DOCUMENTS

2013/0117677 A1* 5/2013 St. Jacques, Jr. ......... G06F 3/00
                                                      715/738
2013/0249903 A1    9/2013 Isokawa et al.

FOREIGN PATENT DOCUMENTS

| JP | 2009-70201 A | 4/2009 |
| JP | 2011-083590 A | 4/2011 |
| JP | 2015-191581 A | 11/2015 |
| JP | 2017-204041 A | 11/2017 |
| WO | WO 2012/049741 A1 | 4/2012 |

* cited by examiner

FIG.7

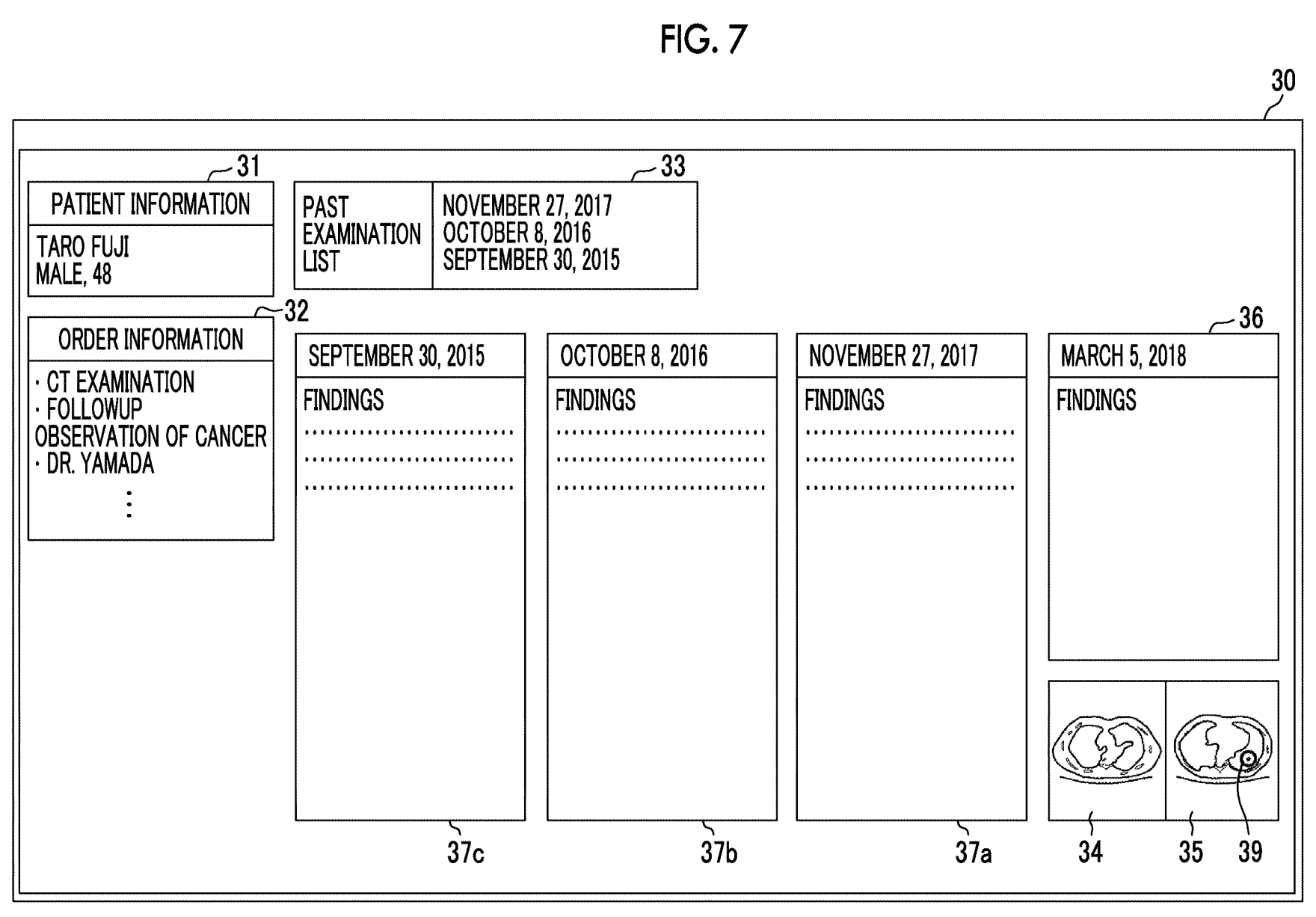

| PATIENT INFORMATION | |
|---|---|
| TARO FUJI MALE, 48 | |

| ORDER INFORMATION | |
|---|---|
| · CT EXAMINATION<br>· FOLLOWUP<br>· OBSERVATION OF CANCER<br>· DR. YAMADA<br>· · · | |

| PAST EXAMINATION LIST | NOVEMBER 27, 2017<br>OCTOBER 8, 2016<br>SEPTEMBER 30, 2015 |
|---|---|

| SEPTEMBER 30, 2015 |
|---|
| FINDINGS · · · |

37c

| OCTOBER 8, 2016 |
|---|
| FINDINGS · · · |

37b

| NOVEMBER 27, 2017 |
|---|
| FINDINGS · · · |

37a

| MARCH 5, 2018 |
|---|
| FINDINGS |

37a
NOVEMBER 27, 2017
FINDINGS
A WITH SIZE S IS RECOGNIZED AT PART a. THERE IS B AT PART b. — 40
THERE IS NO SIGNIFICANT CHANGE IN C.
DIAGNOSIS
..........
..........

37b
NOVEMBER 27, 2017
FINDINGS
A IS RECOGNIZED AT PART a.
THERE IS D AT C.
DIAGNOSIS
..........
..........

37c
NOVEMBER 27, 2017
FINDINGS
THERE IS B AT PART b. — 40
DIAGNOSIS
..........
..........

FINDINGS
A WITH SIZE S IS RECOGNIZED AT PART a. THERE IS B AT PART b.
THERE IS NO SIGNIFICANT CHANGE IN C.

DIAGNOSIS
......
......

40

37b

NOVEMBER 27, 2017

FINDINGS
A IS RECOGNIZED AT PART a.
THERE IS D AT C.

DIAGNOSIS
......
......

NO SPECIFIC CHARACTER — 42

37c

NOVEMBER 27, 2017

FINDINGS
THERE IS B AT PART b.

DIAGNOSIS
......
......

40

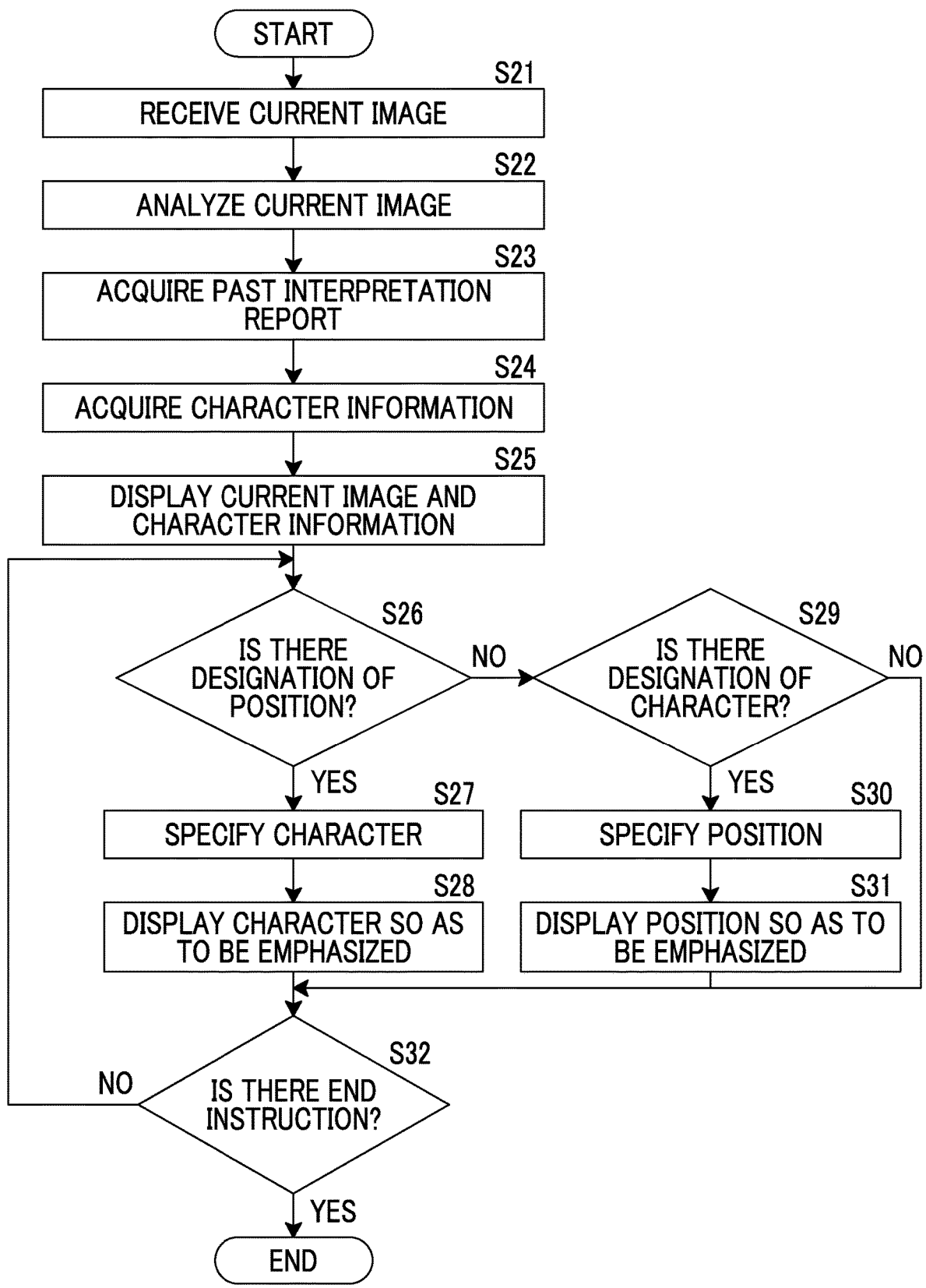

MEDICAL IMAGE PROCESSING APPARATUS, MEDICAL IMAGE PROCESSING METHOD, AND MEDICAL IMAGE PROCESSING PROGRAM

CROSS REFERENCE TO RELATED APPLICATIONS

The present application claims priority under 35 U.S.C. § 119 to Japanese Patent Application No. 2018-040202 filed on Mar. 6, 2018. The above application is hereby expressly incorporated by reference, in its entirety, into the present application.

BACKGROUND

1. Technical Field

The present invention relates to a medical image processing apparatus, a medical image processing method, and a medical image processing program.

2. Description of the Related Art

In recent years, advances in medical apparatuses, such as computed tomography (CT) apparatuses and magnetic resonance imaging (MRI) apparatuses, have enabled image diagnosis using high-resolution three-dimensional medical images with higher quality. In particular, since a region of a lesion can be accurately specified by image diagnosis using CT images, MRI images, and the like, appropriate treatment can be performed based on the specified result.

A medical image is analyzed by computer aided diagnosis (CAD) using a discriminator learned by deep learning or the like, regions, positions, volumes, and the like of lesions included in the medical image are extracted, and these are acquired as the analysis result. The analysis result generated by analysis processing in this manner is stored in a database so as to be associated with examination information, such as a patient name, gender, age, and a modality that has acquired the medical image, and provided for diagnosis. The radiologist interprets the medical image with reference to the transmitted medical image and analysis result and creates an interpretation report in his or her own interpretation terminal device.

An interpretation report on a three-dimensional medical image is stored in an image server or the like so as to be associated with a medical image referred to at the time of creating the interpretation report among a plurality of two-dimensional medical images forming the three-dimensional medical image. For this reason, by referring to the past interpretation report, it is possible to specify a medical image referred to at the time of creating the past interpretation report (hereinafter, referred to as a past image). Therefore, a current image acquired in the current examination and a past image acquired in the past examination can be simultaneously displayed on the interpretation terminal device of the radiologist. By performing interpretation while comparing the current image with the past image, the radiologist can easily check that the contents mentioned in the past interpretation report are contents corresponding to which position of the current image and check how the position of interest in the current image is mentioned in the past interpretation report. Therefore, the interpretation efficiency is good.

On the other hand, various methods have been proposed for referring to medical images referred to at the time of creating the past interpretation report, that is, past images, at the time of creating the current interpretation report. For example, JP2009-070201A has proposed a method of creating correspondence information, in which a plurality of past images having different imaging positions and a plurality of current images having different imaging positions are associated with each other for each imaging position, and creating a template for the current interpretation report based on the created correspondence information and the past interpretation report.

SUMMARY

However, there is a case in which an interpretation report is not associated with a medical image, which was referred to at the time of creating the interpretation report, on the system because the creation time is old and the like. In such a case, it is difficult to specify and display a medical image referred to at the time of creating the interpretation report, that is, the past image. In particular, since a three-dimensional medical image such as a CT image and an MRI image is configured to include a number of tomographic images, it is very difficult to specify which tomographic image has been referred to in order to create the interpretation report.

The invention has been made in view of the above circumstances, and it is an object of the invention to improve the interpretation efficiency without referring to past images.

A first medical image processing apparatus according to the invention comprises: an image receiving unit that receives a current image acquired by imaging a subject; a character information acquisition unit that acquires character information from past medical information relevant to the current image; a position receiving unit that receives a designation of a position in the current image received by the image receiving unit; a character specifying unit that specifies a character relevant to the position received by the position receiving unit from the character information acquired by the character information acquisition unit; and a display control unit that performs control to display the character specified by the character specifying unit so as to be emphasized on a display unit.

A second medical image processing apparatus according to the invention comprises: an image receiving unit that receives a current image acquired by imaging a subject; a character information acquisition unit that acquires character information from past medical information relevant to the current image; a character receiving unit that receives a designation of a character in the character information acquired by the character information acquisition unit; a position specifying unit that specifies a position relevant to the character received by the character receiving unit in the current image received by the image receiving unit; and a display control unit that performs control to display the position specified by the position specifying unit so as to be emphasized on a display unit.

A third medical image processing apparatus according to the invention comprises: an image receiving unit that receives a current image acquired by imaging a subject; a character information acquisition unit that acquires character information from past medical information relevant to the current image; a position receiving unit that receives a designation of a position in the current image received by the image receiving unit; a character receiving unit that receives a designation of a character in the character information acquired by the character information acquisition unit; a character specifying unit that specifies a character relevant to the position received by the position receiving unit from the character information acquired by the character information acquisition unit in a case where the designation of the position is received by the position receiving unit; a position specifying unit that specifies a position relevant to the character received by the character receiving unit in the current image received by the image receiving unit in a case where the designation of the character is received by the character receiving unit; and a display control unit that performs control to display the specified character so as to be emphasized on a display unit in a case where the character is specified by the character specifying unit and performs control to display the specified position so as to be emphasized on the display unit in a case where the position is specified by the position specifying unit.

In the first and third medical image processing apparatuses according to the invention, in a case where a plurality of the characters are specified by the character specifying unit, the display control unit may perform control to display the characters so as to be emphasized by weighting according to contents of the characters.

In the second and third medical image processing apparatuses according to the invention, in a case where a plurality of the positions are specified by the position specifying unit, the display control unit may perform control to display the positions so as to be emphasized by weighting according to the positions.

In the medical image processing apparatus according to the invention, in a case where the character specifying unit does not specify a character relevant to the position received by the position receiving unit in the character information acquired from first past medical information and specifies the character in the character information acquired from second past medical information before the first past medical information, the display control unit may perform control to display the character, which is specified in the second past character information by the character specifying unit, so as to be emphasized on the display unit and control a notification unit to notify that the character has not been specified in the first past medical information.

In the medical image processing apparatus according to the invention, in a case where the character information acquisition unit acquires the character information in a plurality of pieces of the past medical information, the display control unit may perform control to display the character information for each of different pieces of the past medical information in a display method based on any one of parallel display, individual display, or overlapping display.

In the medical image processing apparatus according to the invention, the character may include feature information indicating a feature of a lesion.

A first medical image processing method according to the invention comprises: receiving a current image acquired by imaging a subject; acquiring character information from past medical information relevant to the current image; receiving a designation of a position in the received current image; specifying a character relevant to the received position from the acquired character information; and performing control to display the specified character so as to be emphasized on a display unit.

A second medical image processing method according to the invention comprises: receiving a current image acquired by imaging a subject; acquiring character information from past medical information relevant to the current image; receiving a designation of a character in the acquired character information; specifying a position relevant to the received character in the received current image; and performing control to display the specified position so as to be emphasized on a display unit.

A third medical image processing method according to the invention comprises: receiving a current image acquired by imaging a subject; acquiring character information from past medical information relevant to the current image; receiving a designation of a position in the received current image or receiving a designation of a character in the acquired character information; specifying a character relevant to the received position from the acquired character information in a case where the designation of the position is received and performing control to display the specified character so as to be emphasized on a display unit; and specifying a position relevant to the received character in the received current image in a case where the designation of the character is received and performing control to display the specified position so as to be emphasized on the display unit.

In addition, a program causing a computer to execute the medical image processing method according to the invention may be provided.

A first medical image processing program of the invention causes a computer to execute: a step of receiving a current image acquired by imaging a subject; a step of acquiring character information from past medical information relevant to the current image; a step of receiving a designation of a position in the received current image; a step of specifying a character relevant to the received position from the acquired character information; and a step of performing control to display the specified character so as to be emphasized on a display unit.

A second medical image processing program of the invention causes a computer to execute: a step of receiving a current image acquired by imaging a subject; a step of acquiring character information from past medical information relevant to the current image; a step of receiving a designation of a character in the acquired character information; a step of specifying a position relevant to the received character in the received current image; and a step of performing control to display the specified position so as to be emphasized on a display unit.

A third medical image processing program of the invention causes a computer to execute: a step of receiving a current image acquired by imaging a subject; a step of acquiring character information from past medical information relevant to the current image; a step of receiving a designation of a position in the received current image or receiving a designation of a character in the acquired character information; a step of specifying a character relevant to the received position from the acquired character information in a case where the designation of the position is received and performing control to display the specified character so as to be emphasized on a display unit; and a step of specifying a position relevant to the received character in the received current image in a case where the designation of the character is received and performing control to display the specified position so as to be emphasized on the display unit.

Another first medical image processing apparatus according to the invention comprises: a memory that stores commands to be executed by a computer; and a processor configured to execute the stored commands. The processor executes: a step of receiving a current image acquired by imaging a subject; a step of acquiring character information from past medical information relevant to the current image; a step of receiving a designation of a position in the received current image; a step of specifying a character relevant to the received position from the acquired character information;

and a step of performing control to display the specified character so as to be emphasized on a display unit.

Another second medical image processing apparatus according to the invention comprises: a memory that stores commands to be executed by a computer; and a processor configured to execute the stored commands. The processor executes: a step of receiving a current image acquired by imaging a subject; a step of acquiring character information from past medical information relevant to the current image; a step of receiving a designation of a character in the acquired character information; a step of specifying a position relevant to the received character in the received current image; and a step of performing control to display the specified position so as to be emphasized on a display unit.

Another third medical image processing apparatus according to the invention comprises: a memory that stores commands to be executed by a computer; and a processor configured to execute the stored commands. The processor executes: a step of receiving a current image acquired by imaging a subject; a step of acquiring character information from past medical information relevant to the current image; a step of receiving a designation of a position in the received current image or receiving a designation of a character in the acquired character information; a step of specifying a character relevant to the received position from the acquired character information in a case where the designation of the position is received and performing control to display the specified character so as to be emphasized on a display unit; and a step of specifying a position relevant to the received character in the received current image in a case where the designation of the character is received and performing control to display the specified position so as to be emphasized on the display unit.

According to the first medical image processing apparatus, the first medical image processing method, and the first medical image processing program of the invention, the designation of a position in the current image is received, characters relevant to the received position are specified from the character information among the pieces of past medical information relevant to the current image, and the specified characters are displayed so as to be emphasized. Therefore, since it is possible to easily check how the position of interest in the current image is mentioned in the past medical information, the interpretation efficiency is improved.

According to the second medical image processing apparatus, the second medical image processing method, and the second medical image processing program of the invention, the designation of a character in the character information among the pieces of past medical information relevant to the current image is received, a position relevant to the received character is specified in the current image, and the specified position is displayed so as to be emphasized. Therefore, since it is possible to easily check that the contents mentioned in the past medical information are contents corresponding to which position of the current image, the interpretation efficiency is improved.

According to the third medical image processing apparatus, the third medical image processing method, and the third medical image processing program of the invention, in a case where the designation of a position in the current image is received, characters relevant to the received position are specified from the character information among the pieces of past medical information relevant to the current image, and the specified characters are displayed so as to be emphasized. In addition, in a case where the designation of a character in the character information among the pieces of past medical information relevant to the current image is received, a position relevant to the received character is specified in the current image, and the specified position is displayed so as to be emphasized. Therefore, since it is possible to easily check how the position of interest in the current image is mentioned in the past medical information and easily check that the contents mentioned in the past medical information are contents corresponding to which position of the current image, the interpretation efficiency is improved.

BRIEF DESCRIPTION OF THE DRAWINGS

FIG. 7 is a diagram showing another example of an interpretation report screen.

FIG. 9 is a diagram illustrating a different past interpretation report.

FIG. 10 is a diagram illustrating an example of a notification unit.

FIG. 16 is a flowchart showing medical image processing performed in the third embodiment.

DETAILED DESCRIPTION

Figure 1:
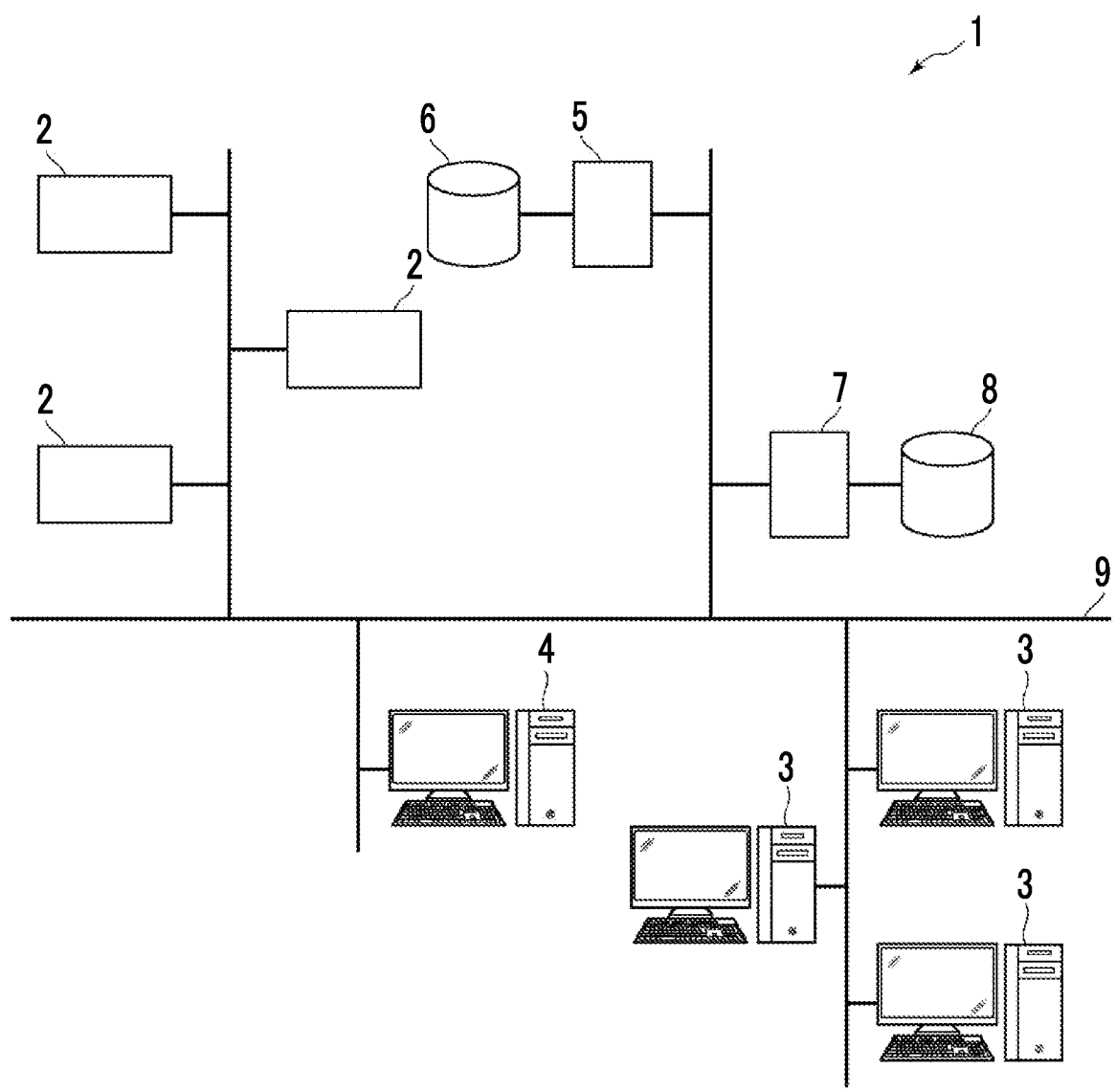
FIG. 1 is a diagram showing the schematic configuration of a medical information system to which a medical image processing apparatus according to an embodiment of the invention is applied.

Hereinafter, an embodiment of the invention will be described with reference to the accompanying diagrams. FIG. 1 is a diagram showing the schematic configuration of a medical information system to which a medical image processing apparatus according to a first embodiment of the invention is applied. A medical information system 1 shown in FIG. 1 is a system for performing imaging of an examination target part of a subject, storage of a medical image acquired by imaging, interpretation of a medical image by a radiologist and creation of an interpretation report, and viewing of an interpretation report by a doctor in a medical department of a request source and detailed observation of a medical image to be interpreted, based on an examination order from a doctor in a medical department using a known ordering system. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed onto the computer from the recording medium. Alternatively, the application program is stored in a storage device of a server computer connected to the network 9 or in a network storage so as to be accessible from the outside, and is downloaded and installed onto the computer as necessary.

The modality 2 is an apparatus that generates a medical image showing a diagnosis target part by imaging the diagnosis target part of the subject. Specifically, the modality 2 is a simple X-rays imaging apparatus, a CT apparatus, an MRI apparatus, a positron emission tomography (PET) apparatus, and the like. A medical image generated by the modality 2 is transmitted to the image server 5 and stored therein.

The interpretation WS 3 includes the medical image processing apparatus according to the first embodiment. The configuration of the interpretation WS 3 will be described later.

The medical department WS 4 is a computer used by a doctor in a medical department to observe the details of an image, view an interpretation report, create an electronic medical record, and the like, and is configured to include a processing device, a display device such as a display, and an input device such as a keyboard and a mouse. In the medical department WS 4, each process, such as creation of a patient's medical record (electronic medical record), sending a request to view an image to the image server 5, display of an image received from the image server 5, automatic detection or highlighting of a lesion-like portion in an image, sending a request to view an interpretation report to the interpretation report server 7, and display of an interpretation report received from the interpretation report server 7, is performed by executing a software program for each process.

The image server 5 is obtained by installing a software program for providing a function of a database management system (DBMS) on a general-purpose computer. The image server 5 comprises a storage for an image database 6. This storage may be a hard disk device connected to the image server 5 by a data bus, or may be a disk device connected to a storage area network (SAN) or a network attached storage (NAS) connected to the network 9. In a case where the image server 5 receives a request to register a medical image from the modality 2, the image server 5 registers the medical image in the image database 6 in a format for a database.

Medical images acquired by the modality 2 or image data of a medical image group including a plurality of medical images and accessory information are registered in the image database 6. The accessory information includes, for example, an image ID for identifying each medical image or a medical image group (hereinafter, may be simply referred to as a medical image), a patient identification (ID) for identifying a subject, an examination ID for identifying an examination, a unique ID (UID: unique identification) allocated for each medical image, examination date and examination time at which the medical image or the medical image group is generated, the type of a modality used in an examination for acquiring a medical image, patient information such as patient's name, age, and gender, an examination part (imaging part), imaging information (an imaging protocol, an imaging sequence, an imaging method, imaging conditions, the use of a contrast medium, and the like), and information such as a series number or a collection number in a case where a plurality of medical images are acquired in one examination.

In a case where a viewing request from the interpretation WS 3 is received through the network 9, the image server 5 searches for a medical image registered in the image database 6 and transmits the searched medical image to the interpretation WS 3 that is a request source.

The interpretation report server 7 has a software program for providing a function of a database management system to a general-purpose computer. In a case where the interpretation report server 7 receives a request to register an interpretation report from the interpretation WS 3, the interpretation report server 7 registers the interpretation report in the interpretation report database 8 in a format for a database. In a case where a request to search for an interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and the certainty factor of findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated circuit. In any case, it is preferable that the network 9 is configured to be able to realize high-speed transmission of medical images, such as an optical network.

Hereinafter, the interpretation WS 3 according to the present embodiment will be described in detail. The interpretation WS 3 is a computer used by a radiologist of a medical image to interpret the medical image and create the interpretation report, and is configured to include a processing device, a display device such as a display, and an input device such as a keyboard and a mouse. In the interpretation WS 3, each process, such as making a request to view a medical image to the image server 5, various kinds of image processing on a medical image received from image server 5, display of a medical image, analysis processing on a medical image, highlighting of a medical image based on the analysis result, creation of an interpretation report based on the analysis result, support for the creation of an interpretation report, making a request to register an interpretation report and a request to view an interpretation report to the interpretation report server 7, and display of an interpretation report received from the interpretation report server 7, is performed by executing a software program for each process. Since processes other than the process performed by the medical image processing apparatus of the present embodiment, among these processes, are performed by a known software program, the detailed description thereof will be omitted herein. The processes other than the process performed by the medical image processing apparatus of the present embodiment may not be performed in the interpretation WS 3, and a computer that performs the processes may be separately connected to the network 9, and requested processing on the computer may be performed according to a processing request from the interpretation WS 3.

The interpretation WS 3 includes the medical image processing apparatus according to the first embodiment. Therefore, a medical image processing program according to the first embodiment is installed on the interpretation WS 3. The medical image processing program is recorded on a recording medium, such as a DVD or a CD-ROM, and distributed, and is installed onto the interpretation WS 3 from the recording medium. Alternatively, the medical image processing program is stored in a storage device of a server computer connected to the network or in a network storage so as to be accessible from the outside, and is downloaded and installed onto the interpretation WS 3 as necessary.

Figure 2:
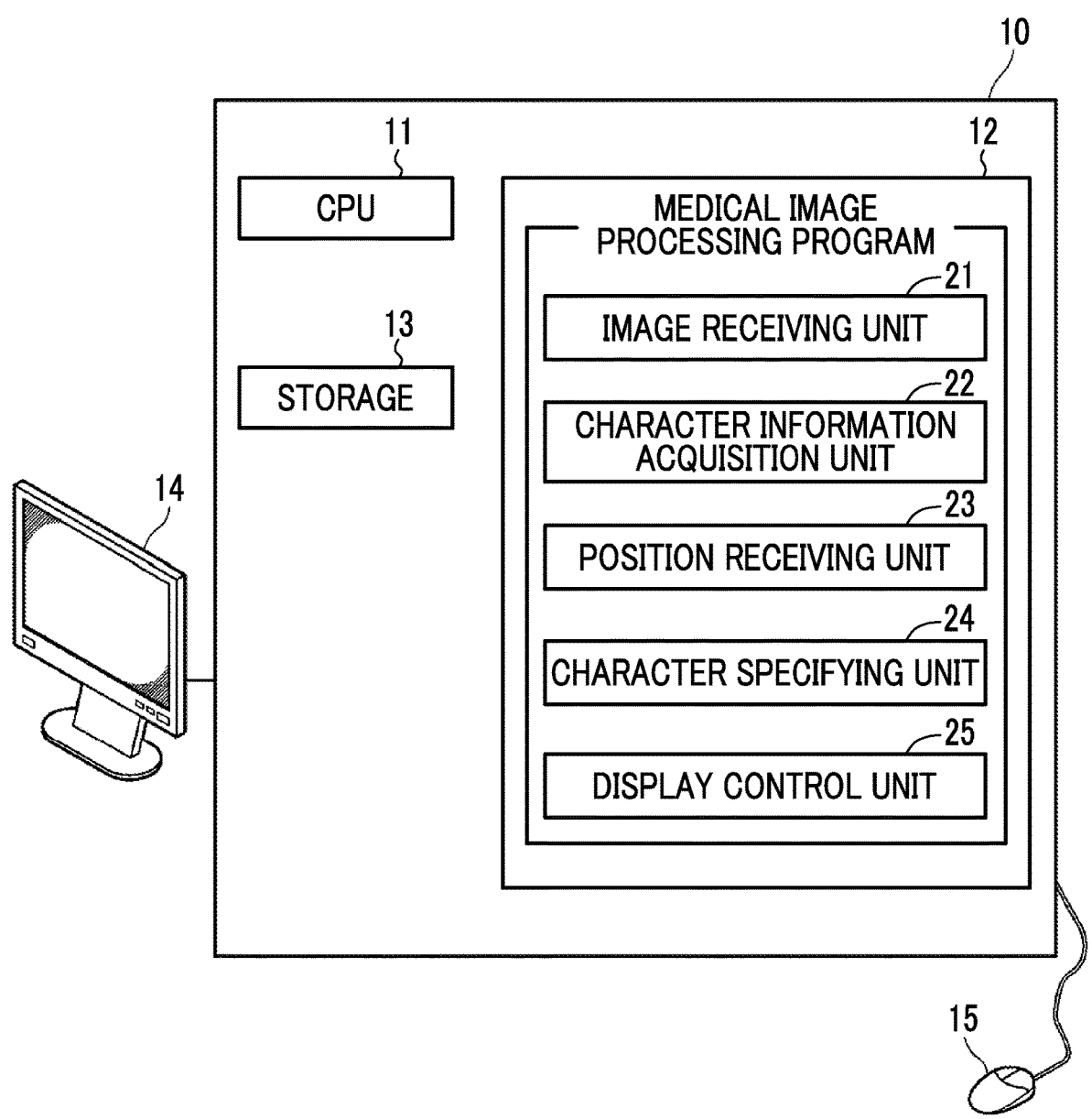
FIG. 2 is a diagram showing the schematic configuration of a medical image processing apparatus according to a first embodiment.

FIG. 2 is a diagram showing the schematic configuration of a medical image processing apparatus 10 according to the first embodiment of the invention that is realized by installing the medical image processing program. As shown in FIG. 2, a medical image processing apparatus 10 comprises a central processing unit (CPU) 11, a memory 12, and a storage 13 as the configuration of a standard computer. A display device (hereinafter, referred to as a display unit) 14, such as a liquid crystal display, and an input device (hereinafter, referred to as an input unit) 15, such as a keyboard and a mouse, are connected to the medical image processing apparatus 10.

The storage 13 is a storage device, such as a hard disk or a solid state drive (SSD). Medical images and various kinds of information including information necessary for processing of the medical image processing apparatus 10, which are acquired from the image server 5 through the network 9, are stored in the storage 13.

A medical image processing program is stored in the memory 12. As processing to be executed by the CPU 11, the medical image processing program defines: image receiving processing for receiving a current image acquired by imaging a subject; character information acquisition processing for acquiring character information from past medical information relevant to the current image; position receiving processing for receiving a designation of a position in the received current image; character specifying processing for specifying a character relevant to the received position from the acquired character information; and display control processing for performing control to display the specified character on a display unit so as to be emphasized.

The CPU 11 executes these processes according to the medical image processing program, so that the computer functions as an image receiving unit 21, a character information acquisition unit 22, a position receiving unit 23, a character specifying unit 24, and a display control unit 25. In the first embodiment, the CPU 11 executes the function of each unit according to the medical image processing program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor. As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

The image receiving unit 21 receives a current image acquired by imaging the subject. In the present embodiment, the "current image" is an image to be referred to at the time of creating an interpretation report, and a plurality of tomographic images forming a three-dimensional image correspond to the current image. In the present embodiment, it is assumed that a three-dimensional image is a CT image of a thoracoabdominal portion. Specifically, the interpretation WS 3 instructs the image server 5 to transmit a CT image that is a target of an interpretation report to be created by the radiologist this time. In a case where a viewing request from the interpretation WS 3 is received through the network 9, the image server 5 searches for a medical image registered in the image database 6 and transmits the searched medical image, that is, a CT image, to the interpretation WS 3 that is a request source. The image receiving unit 21 receives the CT image transmitted from the image server 5. The CT image received by the image receiving unit 21 is stored in the storage 13. By acquiring the CT image, the image receiving unit 21 can acquire a plurality of tomographic images forming a CT image, that is, a current image.

The character information acquisition unit 22 acquires character information from the past medical information relevant to the current image received by the image receiving unit 21. In the present embodiment, the "medical information" means a medical document, such as an interpretation report, a diagnosis report, and an electronic medical record, and also includes a medical document including information (for example, an image) other than character information. The "past medical information" is past information regarding the same subject as the imaging target subject of the current image. The "character information" means information formed by characters included in the medical information. Since a character string is a group of characters, "characters" in the present embodiment include not only characters but also a character string. "Characters" also include a number, a symbol, and the like.

In order to acquire character information, the character information acquisition unit 22 instructs the interpretation report server 7 to transmit a past interpretation report (hereinafter, may be referred to as a past report) as medical information created for the subject who is an imaging target of the current image received by the image receiving unit 21.

The interpretation report server 7 acquires the requested past report from the interpretation report database 8 and transmits the acquired past report to the interpretation WS 3. The character information acquisition unit 22 acquires characters, which are included in the past report transmitted from the interpretation report server 7, as character information. The past report and the character information received by the character information acquisition unit 22 are stored in the storage 13.

The position receiving unit 23 receives designation of the position in the current image received by the image receiving unit 21. As an example, in a current image displayed on a display unit 14, in a case where the radiologist as an operator designates a certain position using an input unit 15, a coordinate position on the CT image indicated by the designated position is acquired.

The character specifying unit 24 specifies characters relevant to the position received by the position receiving unit 23 from the character information acquired by the character information acquisition unit 22. The character specifying unit 24 of the present embodiment includes an analysis unit (not shown) as an example. The analysis unit extracts an anatomical region in the CT image received by the image receiving unit 21, and sets an anatomical part name for each extracted anatomical region. Here, structures included in the thoracoabdominal portion of the human body are lung field, heart, liver, muscle, fat, bone, and the like. The analysis unit extracts structures, such as a lung field region, a heart region, a liver region, and a bone region, from each of a plurality of tomographic images as current images forming a CT image. For example, a part name is set for each extracted anatomical region such that a region A1 is the lung field, a region A2 is the heart, a region A3 is the liver, and a region A4 is the bone. The analysis unit sets each anatomical region so as to match the coordinate position in the CT image. The character specifying unit 24 acquires the part name of a region corresponding to the position received by the position receiving unit 23, that is, the coordinate position.

As a method of setting the part name by the analysis unit, for example, a method described in JP2009-045286A can be used. However, the invention is not limited thereto, and any method may be used as long as the part name can be derived in a case where the position is designated in the image.

In the present embodiment, the character specifying unit 24 includes the analysis unit as an example. However, the invention is not limited thereto. For example, information of the part name of each anatomical region that matches the coordinate position of the CT image can be stored in advance in the image database 6, and the character specifying unit 24 can acquire the information of the part name from the image database 6 and use the acquired information of the part name. In addition, an external analysis server or the like may analyze a CT image.

The character specifying unit 24 further searches for a character relevant to the acquired part name in the character information acquired by the character information acquisition unit 22, and specifies the character detected by the search as a character relevant to the part name. In the present embodiment, for example, in a case where the part name is "lung", the character specifying unit 24 detects the character "lung" from the character information acquired by the character information acquisition unit 22, and specifies a character string including the character "lung" as a character relevant to the lung. For the detection of a character, for example, a similar word search can be used, and a known technique for searching for a character from a sentence can be used. In the present embodiment, a character string including "lung" is specified as a character relevant to "lung". However, the invention is not limited thereto, and only the characters of "lung" may be specified as characters relevant to "lung".

The display control unit 25 performs control to display the character specified by the character specifying unit 24 so as to be emphasized on the display unit 14. The control of the display control unit 25 will be described in detail later.

Figure 3:
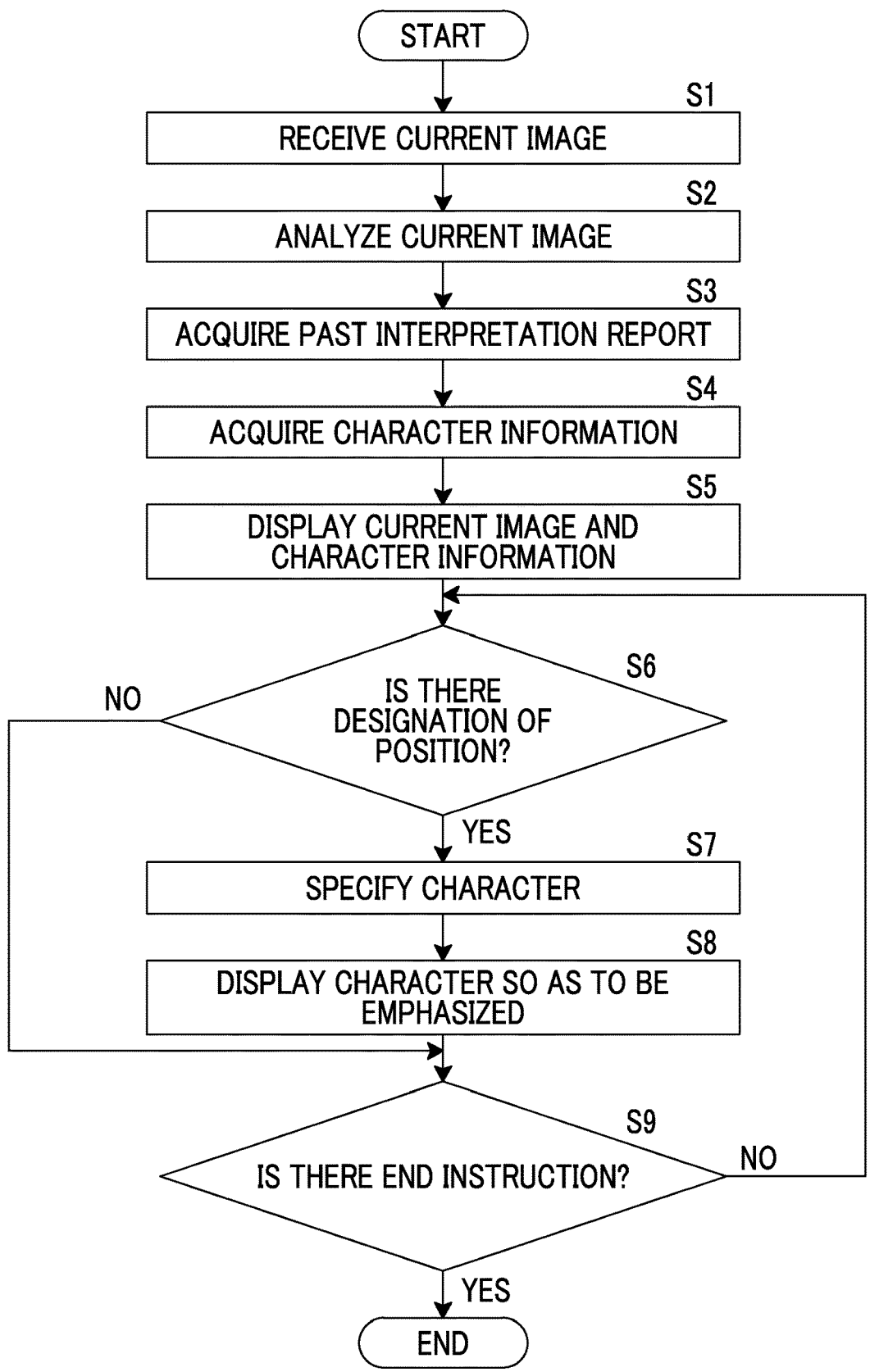
FIG. 3 is a flowchart showing medical image processing performed in the first embodiment.
Figure 4:
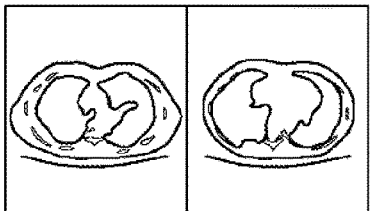
FIG. 4 is a diagram showing an interpretation report screen.
Figure 5:
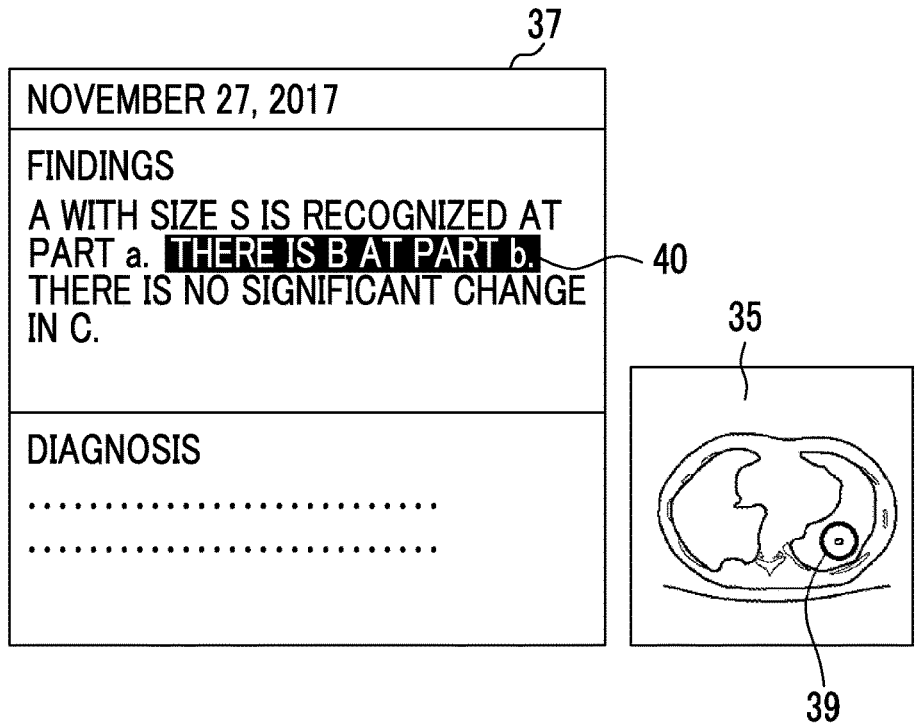
FIG. 5 is a diagram illustrating the designation of a position and the display of characters in a current image.

Next, medical image processing performed in the first embodiment will be described. In the first embodiment, as an example, medical image processing at the time of creating an interpretation report for a CT image acquired for one subject will be described. It is assumed that the interpretation report created herein is a current interpretation report. FIG. 3 is a flowchart showing medical image processing performed in the first embodiment, FIG. 4 is a diagram showing an interpretation report screen, and FIG. 5 is a diagram illustrating the designation of a position and the display of characters in a current image.

First, in step S1, the image receiving unit 21 receives a plurality of tomographic images forming a CT image as a target of medical image processing, that is, current images.

Then, in step S2, the analysis unit of the character specifying unit 24 analyzes the current images received by the image receiving unit 21 in step S2, thereby acquiring the part name of each anatomical region that matches the coordinate position.

Then, the character information acquisition unit 22 acquires a past interpretation report in step S3. The past interpretation report acquired in step S3 is a past interpretation report on the same subject as the imaging target subject of the current image received in step S1.

Then, in step S4, the character information acquisition unit 22 acquires the characters included in the past report as character information as described above.

Then, in step S5, as shown in FIG. 4, the display control unit 25 displays current images 34 and 35 to be interpreted and the character information included in the past interpretation report on an interpretation report creation screen 30. The interpretation report creation screen 30 includes a patient information region 31 for displaying patient information indicating the name, gender, and the like of a patient to be imaged to acquire a CT image, an order information region 32 for displaying information of an examination order for a request for an examination for acquiring a CT image, an examination list region 33 for displaying a past examination list for a patient whose CT image is acquired, current images 34 and 35 to be interpreted, a creation region 36 for inputting a document for creating an interpretation report, a past interpretation report region 37 for displaying a past interpretation report including character information, and a past image region 38 for displaying a past medical image for which the interpretation report displayed in the past interpretation report region 37 was created. The radiologist (operator) who interprets the current images 34 and 35 inputs the sentence of the findings in the creation region 36 using the input unit 15.

Then, in step S6, the position receiving unit 23 determines whether or not there is a designation of a position. Specifically, as shown in FIG. 5, as an example, a circle cursor 39 for designating a position by the radiologist is displayed so as to overlap the current image 35, and the radiologist moves the circle cursor 39 to a desired position by operating the input unit 15. After moving the cursor 39, the radiologist completes the designation of the position, for example, by left-clicking a mouse as the input unit 15, and the position receiving unit 23 receives the designation of the position. In a case where there is a designation of a position by the radiologist in step S6 (step S6; YES), the position receiving unit 23 receives the designation of the position by the radiologist and acquires the coordinate position of the region of the cursor 39, that is, in the circle on the current image.

In the first embodiment, a circle is used as the cursor 39. However, the invention is not limited thereto. For example, an arrow may be used, or other marks may be used. The size of the cursor 39 is not particularly limited, and can be appropriately set and changed by the operator.

Then, in step S7, the character specifying unit 24 specifies characters relevant to the position received by the position receiving unit 23 from the character information acquired by the character information acquisition unit 22 as described above. In the first embodiment, as an example, as shown in FIG. 5, it is assumed that the coordinate position on the current image of the position received by the position receiving unit 23 is a coordinate position in the region of a part b. In this case, the character specifying unit 24 acquires "part b" as a part name of the region corresponding to the position received by the position receiving unit 23.

Then, the character specifying unit 24 further searches for characters relevant to "part b" in the character information acquired by the character information acquisition unit 22. In the first embodiment, as an example, as shown in FIG. 5, a character string 40 of "There is B at part b." in the past interpretation report on Nov. 27, 2017 is specified as characters relevant to the position received by the position receiving unit 23, that is, the part b. In addition, the character specifying unit 24 searches for characters relevant to "part b" in all the past examination lists displayed in the examination list region 33.

Then, in step S8, the display control unit 25 performs control to display the character string 40 of "There is B at part b." specified by the character specifying unit 24 so as to be emphasized on the display unit 14. Specifically, as shown in FIG. 5, the display control unit 25 displays the character string 40 of "There is B at part b." so as to be emphasized more than other characters by highlighting the character string 40 of "There is B at part b." in the character information displayed in the past interpretation report region 37. As an example, in a case where the radiologist selects the date on Oct. 8, 2016 or Oct. 8, 2015 displayed in the past examination list region 33 by operating the input unit 15, the interpretation report of the selected date is displayed in the past interpretation report region 37. In a case where there is a character specified by the character specifying unit 24 in the displayed interpretation report, the specified character is displayed so as to be emphasized by the display control unit 25 in the same manner as described above.

In the first embodiment, the display control unit 25 displays a character to be emphasized by highlighting the character. However, the invention is not limited thereto. For example, each character of the character string 40 of "There is B at part b." may be displayed in a bold letter rather than other characters, or the character string 40 of "There is B at part b." may be displayed so as to be surrounded by a frame, or the character string 40 of "There is B at part b." may be displayed in a color different from other characters. The method of emphasis display can be set and changed by the operator.

On the other hand, in a case where there is no designation of a position by the radiologist in step S6 (step S6; NO), that is, in a case where the position receiving unit 23 has not received a position, the CPU 11 proceeds to step S9.

Then, in step S9, the CPU 11 determines whether or not there is an end instruction in the interpretation WS 3. In a case where there is no end instruction (step S9; NO), the CPU 11 proceeds to step S6 to continue the process from step S6. In a case where there is an end instruction (step S9; YES), the CPU 11 ends the process.

As described above, in the first embodiment, in a case where the radiologist designates the part b by operating the cursor 39 in the current image 35, the character string 40 of "There is B at part b." is displayed as characters relevant to the part b so as to be emphasized in the character information of the past interpretation report. Therefore, the radiologist can easily visually recognize the characters displayed so as to be emphasized, that is, the character string 40 of "There is B at part b.", on the display unit 14. As a result, since the radiologist can easily check the contents of the findings in the past interpretation report for the part b, the interpretation efficiency is improved. In addition, at the time of creating the current interpretation report, the radiologist can create the findings with reference to the past finding contents for the part b.

Figure 6:
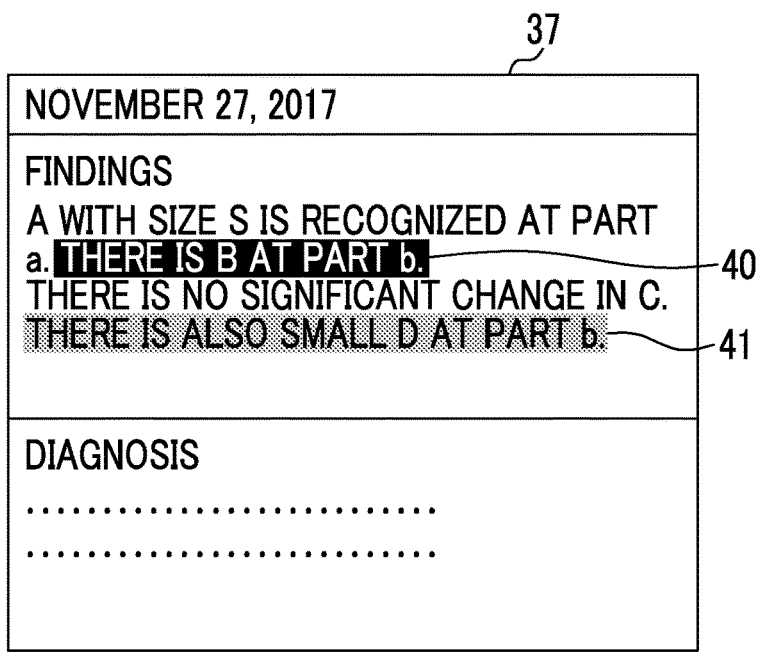
FIG. 6 is a diagram illustrating another example of displaying characters.

In the first embodiment described above, the character specifying unit 24 specifies the character string 40 of "There is B at part b." as characters relevant to the part b. However, the invention is not limited thereto, and the character specifying unit 24 may specify a plurality of character strings. FIG. 6 is a diagram illustrating another example of displaying characters.

As shown in FIG. 6, the character specifying unit 24 specifies the character string 40 of "There is B at part b." and a character string 41 of "There is small D at part b." as characters relevant to the part b. In a case where a plurality of character strings are specified by the character specifying unit 24, the display control unit 25 displays the character strings so as to be emphasized by weighting according to the contents of the character strings 40 and 41. In the first embodiment, characters "small" are included in the character string 41. In the weighting of the size, "small" is determined to be less important than "large" or a sentence whose size is not mentioned. Therefore, as an example, the character string 40 of "There is B at part b." is displayed with a thinner highlight than the character string 41 of "There is small D at part b.". As a result, it is possible to easily visually recognize characters with a high degree of importance.

In the first embodiment described above, the display control unit 25 displays the interpretation report of the date selected by the radiologist, among the dates of Nov. 27, 2017, Oct. 8, 2016, and Sep. 30, 2015, in the past interpretation report region 37. However, the invention is not limited thereto. FIG. 7 is a diagram showing another example of the interpretation report screen, and FIG. 8 is a diagram showing still another example of the interpretation report screen.

As shown in FIG. 7, the display control unit 25 provides past interpretation report regions 37a, 37b, and 37c on the interpretation report creation screen 30 for the interpretation reports of dates 33a, 33b, and 33c, respectively, and displays the character information of the interpretation report of the date corresponding to each region. Therefore, since findings on the part b can be simultaneously checked in time series, the interpretation efficiency is improved.

Figure 8:
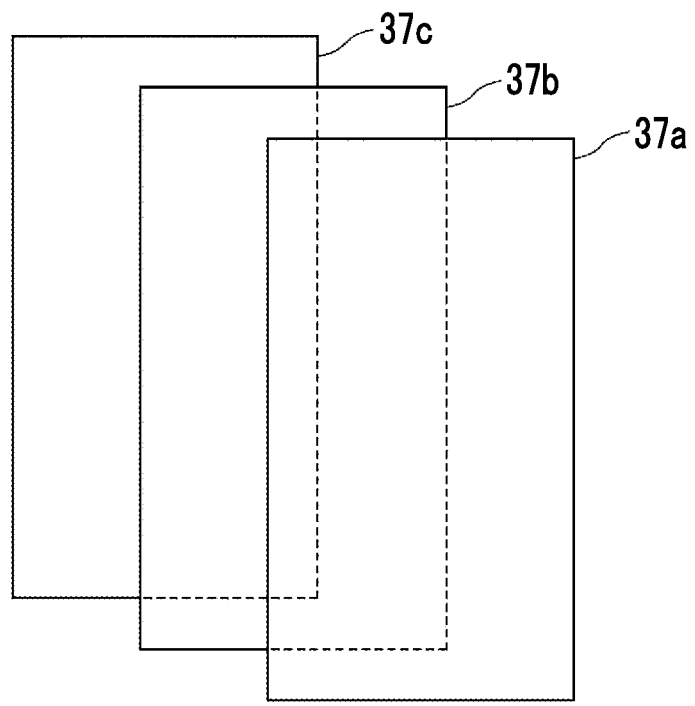
FIG. 8 is a diagram showing still another example of the interpretation report screen.

As shown in FIG. 8, the display control unit 25 provides the past interpretation report regions 37a, 37b, and 37c on the interpretation report creation screen 30 for the interpretation reports of the dates 33a, 33b, and 33c, respectively, so as to at least partially overlap each other, and displays the character information of the interpretation report of the date corresponding to each region. In this case, in a case where the radiologist selects any of the past interpretation report regions 37a, 37b, and 37c by operating the input unit 15, the display control unit 25 displays the selected past interpretation report region at the forefront. Therefore, since the radiologist can easily check the interpretation report of the date that the radiologist desires to check, the interpretation efficiency is improved.

Next, a modification example of the interpretation WS 3 of the first embodiment will be described. The interpretation WS 3 of the first embodiment comprises a notification unit according to the embodiment of the invention in the configuration of the interpretation WS 3 of the first embodiment. Therefore, only the notification unit will be described below, and the description of the other components will be omitted. FIG. 9 is a diagram illustrating different past interpretation reports, and FIG. 10 is a diagram illustrating an example of the notification unit.

As shown in FIG. 9, in a case where the character specifying unit 24 does not specify characters relevant to the part b in the character information acquired from the interpretation report on Oct. 8, 2016 (corresponding to the first past) and specifies "There is B at part b." in the character information acquired from the interpretation report on Sep. 30, 2015 (corresponding to the second past) prior to Oct. 8, 2016, the display control unit 25 performs control to display "There is B at part b.", which is specified in the character information acquired from the interpretation report on Sep. 30, 2015 (corresponding to the second past) by the character specifying unit 24, so as to be emphasized on the display unit 14. Then, the notification unit according to the embodiment of the invention notifies that the characters relevant to the part b have not been specified in the interpretation report on Oct. 8, 2016 in response to an instruction from the display control unit 25.

In the modification example of the interpretation WS 3 of the first embodiment, the notification unit according to the embodiment of the invention is formed by the display unit 14 as an example. The display unit 14 as a notification unit is a display, and displays, for example, a character string 42 of "no specific character" below the interpretation report region 37b on Oct. 8, 2016 on the screen in response to an instruction from the display control unit 25. Therefore, since the character string "There is B at part b." is displayed so as to be emphasized in the interpretation report on Sep. 30, 2015, the radiologist can easily visually recognize that there is B at the part b in the CT image acquired by imaging on Sep. 30, 2015.

In addition, since the character string 42 of "no specific character" is displayed below the interpretation report region 37b on Oct. 8, 2016, the radiologist can easily visually recognize that there is no B at the part b in the CT image acquired by imaging on Oct. 8, 2016. Therefore, since it is possible to easily check the progress of the lesion at the part b, the interpretation efficiency is improved.

In the display unit 14 of the first embodiment described above, the case has been exemplified in which the display control unit 25 visually displays a message or the like indicating that characters relevant to the part b have not been specified on the display so that the radiologist is notified that characters relevant to the part b have not been specified. However, the technique of the invention is not limited thereto. For example, audible display realized by outputting sound using a sound reproduction apparatus or permanent visible display for recording on a recording medium, such as paper, using a printer may be applied. Alternatively, display based on a combination of at least two of visible display using a display, audible display realized by outputting sound using a sound reproduction apparatus, or permanent visible display for recording on a recording medium, such as paper, using a printer may be applied. Alternatively, a notification indicating that characters relevant to the part b have not been specified may be provided by communication means, such as an e-mail or a phone, or a notification indicating that characters relevant to the part b have not been specified may be provided by turning on or blinking an indicator light. At least two or more of the above notification methods may be combined to notify that characters relevant to the part b have not been specified.

Figure 11:
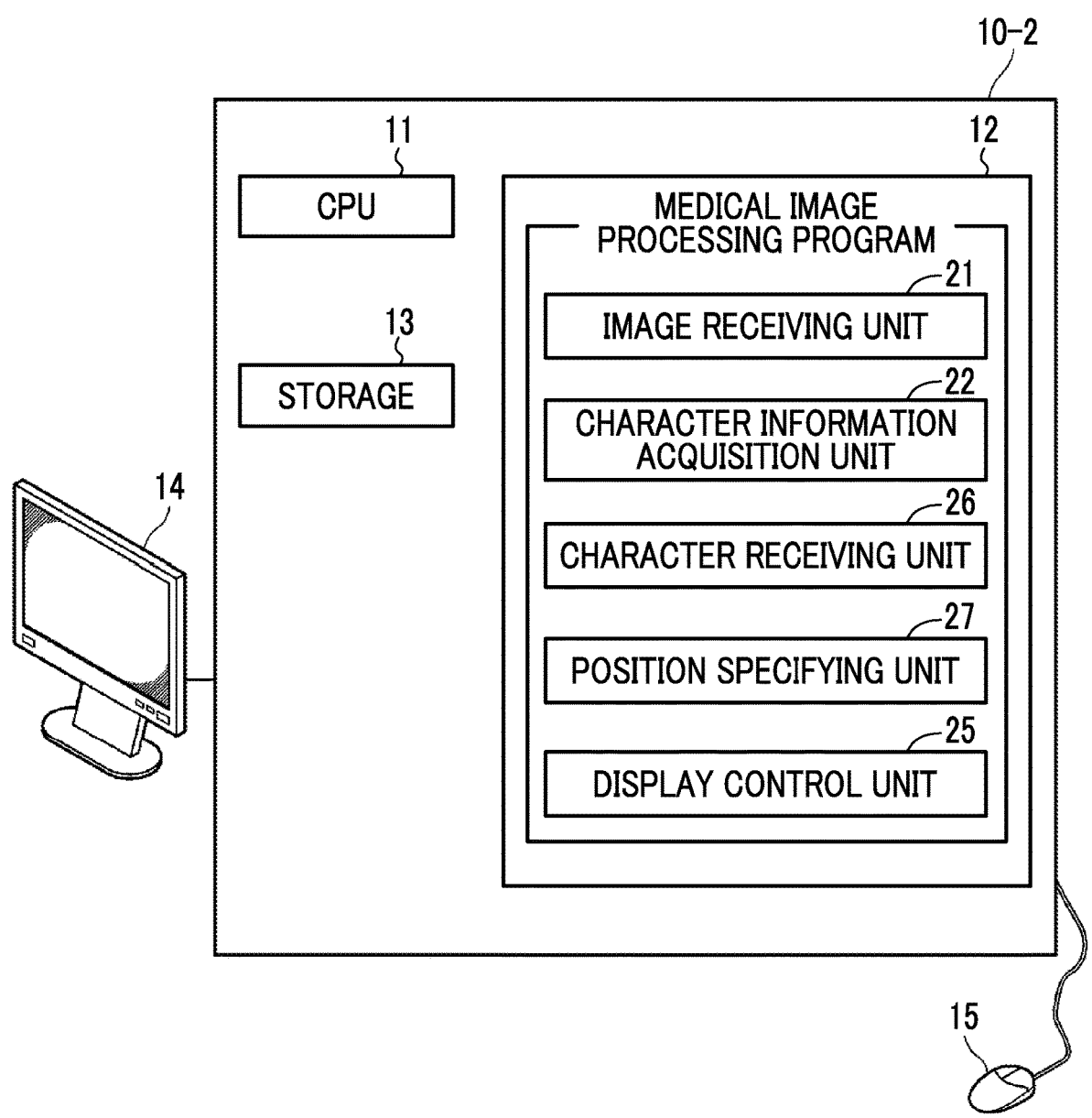
FIG. 11 is a diagram showing the schematic configuration of a medical image processing apparatus according to a second embodiment.

Next, an interpretation WS 3 according to a second embodiment will be described in detail. The interpretation WS 3 according to the second embodiment includes a medical image processing apparatus 10-2 according to the second embodiment. FIG. 11 is a diagram showing the schematic configuration of the medical image processing apparatus 10-2 according to the second embodiment. In FIG. 11, the same components as those in the first embodiment described above are denoted by the same reference numerals, and the description thereof will be omitted herein and only different components will be described in detail.

The medical image processing apparatus 10-2 shown in FIG. 11 does not comprise the position receiving unit 23 and the character specifying unit 24 of the medical image processing apparatus 10 shown in FIG. 2, and includes a character receiving unit 26 and a position specifying unit 27 instead.

The character receiving unit 26 receives designation of characters in the character information acquired by the character information acquisition unit 22. Specifically, as shown in FIG. 5, for example, in a case where the radiologist as an operator designates the character string 40 of "There is B at part b." as desired characters, in the character information displayed in the past interpretation report region 37 of the display unit 14, using the input unit 15, the character receiving unit 26 receives the designated characters.

The position specifying unit 27 specifies a position relevant to the characters received by the character receiving unit 26, that is, the character string 40 of "There is B at part b.", in the current image 35 received by the image receiving unit 21. The position specifying unit 27 of the second embodiment includes an analysis unit (not shown) as an example. Since the analysis unit has the same configuration as the analysis unit included in the character specifying unit 24 of the first embodiment described above, the description thereof will be omitted herein.

The analysis unit extracts an anatomical region in the CT image received by the image receiving unit 21, and sets an anatomical part name for each extracted anatomical region. The position specifying unit 27 acquires a region where the part name of the part b relevant to the characters received by the character receiving unit 26, that is, the character string 40 of "There is B at part b." is set, and specifies a position where the acquired region is shown on the current image 35 as a position relevant to the character string 40 of "There is B at part b.".

In the second embodiment, the position specifying unit 27 includes the analysis unit as an example. However, the invention is not limited thereto. For example, information of the part name of each anatomical region that matches the coordinate position of the CT image can be stored in advance in the image database 6, and the position specifying unit 27 can acquire the information of the part name from the image database 6 and use the acquired information of the part name. In addition, an external analysis server or the like may analyze a CT image.

In the second embodiment, in a case where the character string 40 of "There is B at part b." is designated as an example, a region where the part name of the part b is set is acquired. However, the invention is not limited thereto. For example, a CT image may be analyzed by the CAD using a discriminator learned by deep learning or the like, regions, positions, volumes, and the like of lesions included in the CT image may be extracted, and these may be acquired as the analysis result. In this case, the analysis result generated by analysis processing is stored in the interpretation report database 8 so as to be associated with examination information, such as a patient name, gender, age, and a modality that has acquired the medical image.

For example, in a case where "B" is a character indicating the feature of a lesion, the position specifying unit 27 of the second embodiment searches for the analysis result stored in the interpretation report database 8 through the interpretation report server 7, and acquires the region and the coordinate position of the lesion B included in the CT image. The position specifying unit 27 may specify the coordinate position where the acquired region of the lesion B is present as a position relevant to the character "B".

The position specifying unit 27 of the second embodiment acquires a region where the part name of the part b relevant to the character string 40 of "There is B at part b." is set and the coordinate position where the region of the lesion B is present, and specifies a position where the lesion B located at the part b is shown on the current image 35 as a position relevant to the character string 40 of "There is B at part b." in a case where the lesion B is present in the acquired region.

Figure 12:
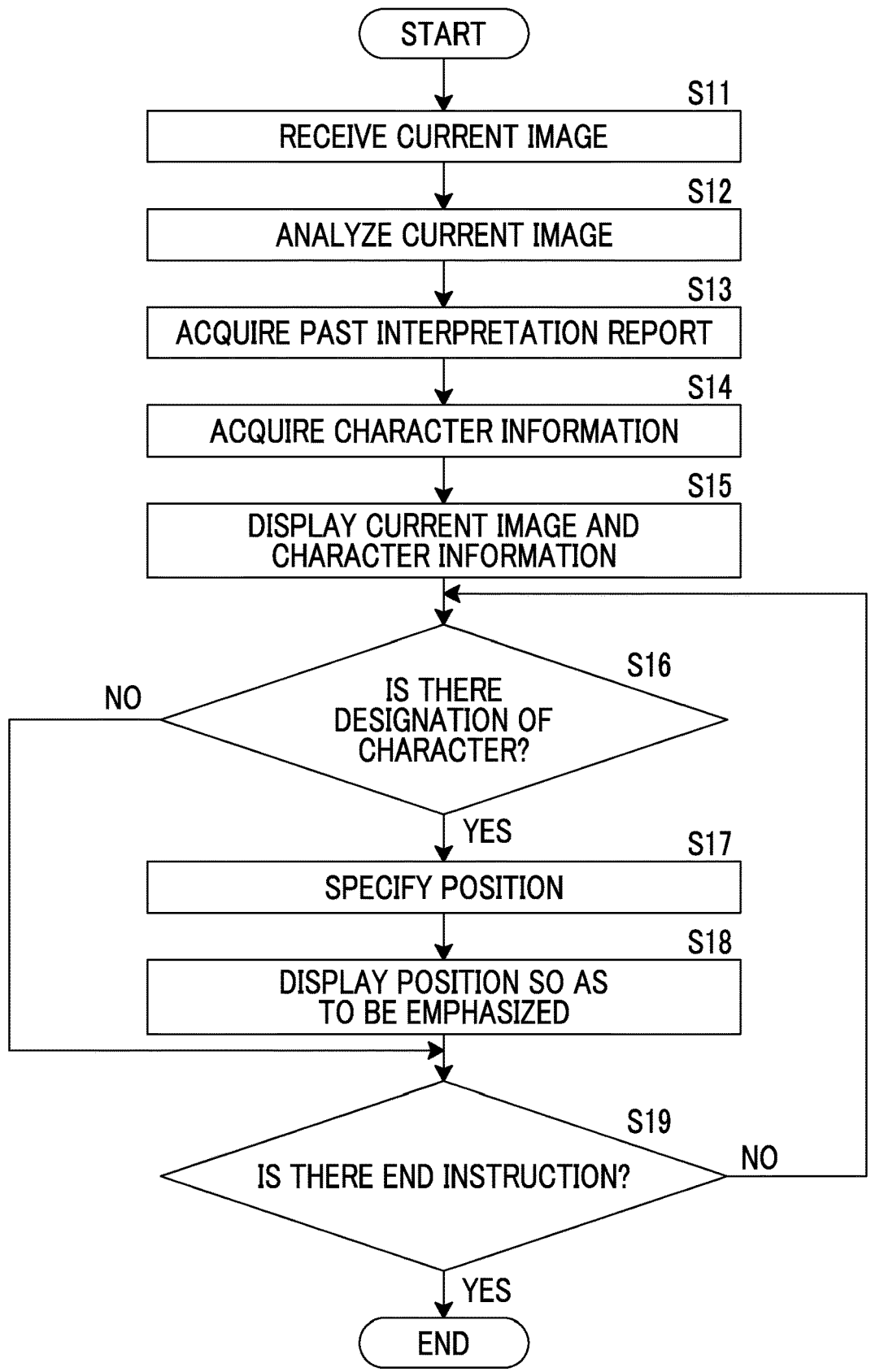
FIG. 12 is a flowchart showing medical image processing performed in the second embodiment.

Next, medical image processing performed in the second embodiment will be described. In the second embodiment, as an example, medical image processing at the time of creating an interpretation report for a CT image acquired for one subject will be described. It is assumed that the interpretation report created herein is a current interpretation report (hereinafter, referred to as a current report). FIG. 12 is a flowchart showing the medical image processing performed in the second embodiment.

Since the processing from step S11 to step S15 in FIG. 12 is the same processing as the processing from step S1 to step S5 in FIG. 3 of the first embodiment described above, the description thereof will be omitted herein.

In step S16, the character receiving unit 26 determines whether or not there is a designation of a character. Specifically, as an example, the cursor 39 for designating a character by the radiologist is displayed so as to overlap the current image 35, and the radiologist moves the cursor 39 to a desired character by operating the input unit 15. After moving the cursor 39 on the desired character, the radiologist selects the character string 40 of "There is B at part b." as shown in FIG. 5 by dragging from the left click position, and the character receiving unit 26 receives the selected character string 40 as designated characters.

Then, in a case where there is a designation of a character by the radiologist in step S16 (step S16; YES), the character receiving unit 26 receives the designation of the character by the radiologist.

In the second embodiment, the above-described method is used in order to select a character string. However, the invention is not limited thereto, and the method of selecting characters can be appropriately set and changed by the operator.

Then, in step S17, as described above, the position specifying unit 27 specifies a position relevant to the characters received by the character receiving unit 26, that is, the character string 40 of "There is B at part b.", in the current image 35 received by the image receiving unit 21. In the second embodiment, as an example, as shown in FIG. 5, the coordinate position on the current image 35 of the lesion B located at the part b is specified as a position relevant to the character string 40 of "There is B at part b.".

Not only for the current image 35 but also for a plurality of tomographic images forming the CT image, for example, the current image 34 shown in FIG. 4, the position specifying unit 27 similarly specifies a position relevant to the characters received by the character receiving unit 26, that is, the character string 40 of "There is B at part b.". Alternatively, the position specifying unit 27 may perform the above-described specification only for the current image set in advance by the radiologist.

Then, in step S18, the display control unit 25 performs control to display the region, which is indicated by the coordinate position on the current image 35 of the lesion B located at the part b specified by the position specifying unit 27, so as to be emphasized on the display unit 14. Specifically, as shown in FIG. 5, the display control unit 25 displays the position relevant to the character string 40 of "There is B at part b." so as to be emphasized more than other parts and other lesions by displaying the lesion B of the part b in the current image 35 displayed in the past interpretation report region 37 so as to be surrounded by a round frame. As an example, in a case where the radiologist selects the date on Oct. 8, 2016 or Oct. 8, 2015 displayed in the past examination list region 33 by operating the input unit 15, the interpretation report of the selected date is displayed in the past interpretation report region 37. Also in the displayed interpretation report, the radiologist designates a desired character string in the character information of the interpretation report, the character receiving unit 26 receives the designated character string, and the position specifying unit 27 specifies a position relevant to the character string received by the character receiving unit 26. Therefore, the specified position is displayed so as to be emphasized by the display control unit 25 in the same manner as described above.

In the second embodiment, the display control unit 25 displays a position to be emphasized, that is, the lesion B of the part b so as to be emphasized by displaying the lesion B of the part b so as to be surrounded by the round frame. However, the invention is not limited thereto. The region of the lesion B of the part b may be displayed in a different color, or may be displayed so as to be surrounded by a frame having a shape other than the round frame. The method of emphasis display can be set and changed by the operator.

On the other hand, in a case where there is no designation of a character by the radiologist in step S16 (step S16; NO), that is, in a case where the character receiving unit 26 has not received a character, the CPU 11 proceeds to step S19.

Then, in step S19, the CPU 11 determines whether or not there is an end instruction in the interpretation WS 3. In a case where there is no end instruction (step S19; NO), the CPU 11 proceeds to step S16 to continue the process from step S16. In a case where there is an end instruction (step S19; YES), the CPU 11 ends the process.

As described above, in the second embodiment, in a case where the radiologist designates the character string 40 of "There is B at part b." as characters by operating the cursor 39 in the character information of the past interpretation report, the region of the lesion B of the part b is displayed as a position relevant to the character string 40 of "There is B at part b." so as to be emphasized in the current image 35. Therefore, the radiologist can easily visually recognize the position displayed so as to be emphasized, that is, the region of the lesion B of the part b, on the display unit 14. As a result, since the radiologist can easily check how "There is B at part b.", which is the finding contents of the past interpretation report, has progressed in the current image, the interpretation efficiency is improved.

Figure 13:
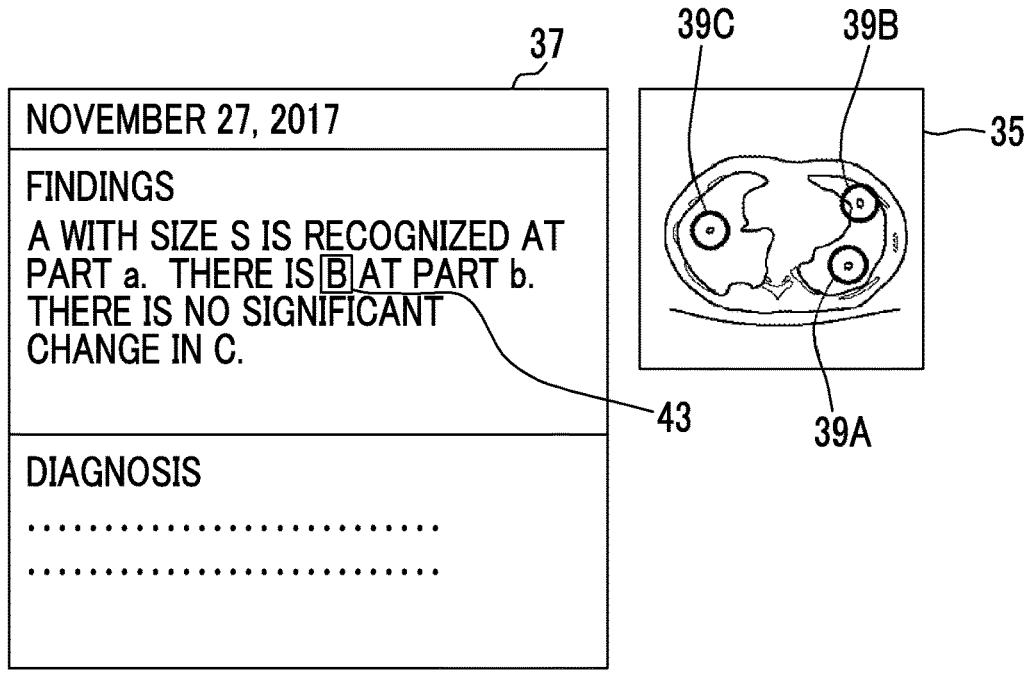
FIG. 13 is a diagram illustrating the designation of characters in the interpretation report and the display of the position of a current image.

In the second embodiment, the character receiving unit 26 of the second embodiment receives the character string 40 of "There is B at part b." as characters. However, the invention is not limited thereto. FIG. 13 is a diagram illustrating the designation of characters in the interpretation report and the display of the position of the current image.

As shown in FIG. 13, the character receiving unit 26 may receive only a character 43 of "B". As an example, in a case where "B" is a lesion, a plurality of lesions B may be present in the current image 35 as shown in FIG. 13. In the present embodiment, three lesions B are present. In this case, the display control unit 25 displays all the three lesions B so as to be emphasized by surrounding the three lesions B with round frames 39A, 39B, and 39C, respectively.

Figure 14:
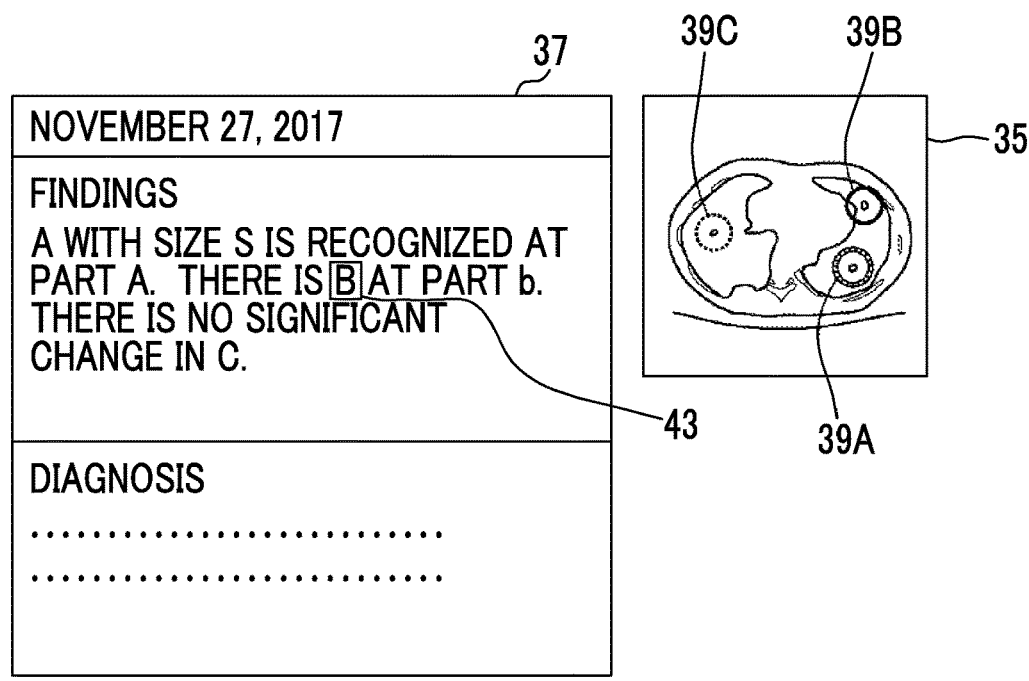
FIG. 14 is a diagram illustrating another example of the designation of characters in the interpretation report and the display of the position of a current image in the second embodiment.

In a case where a plurality of positions of the lesion B are specified by the position specifying unit 27, the display control unit 25 performs control to display the positions so as to be emphasized by weighting according to the position. FIG. 14 is a diagram illustrating another example of the designation of characters in the interpretation report and the display of the position of the current image in the second embodiment.

For example, in a case where the analysis result by the CAD includes the size of the lesion B, the display control unit 25 displays the lesion B so as to be emphasized by weighting according to the size of the region of the lesion B. In the weighting of the size of the region of the lesion B, "small" is determined to be less important than "large" or a sentence whose size is not mentioned. Therefore, as an example, it is assumed that there are the lesion B in the round frame 39A, the lesion B in the round frame 39B, and the lesion B in the round frame 39C in order of the lesion B having a large size. In the second embodiment, as shown in FIG. 14, the display control unit 25 displays the three lesions B with different degrees of emphasis by displaying the round frame 39A as a decorative line, the round frame 39B as a thick line, and the round frame 39C as a one-dot chain line. As a result, it is possible to easily visually recognize the lesion B with a high degree of importance.

Figure 15:
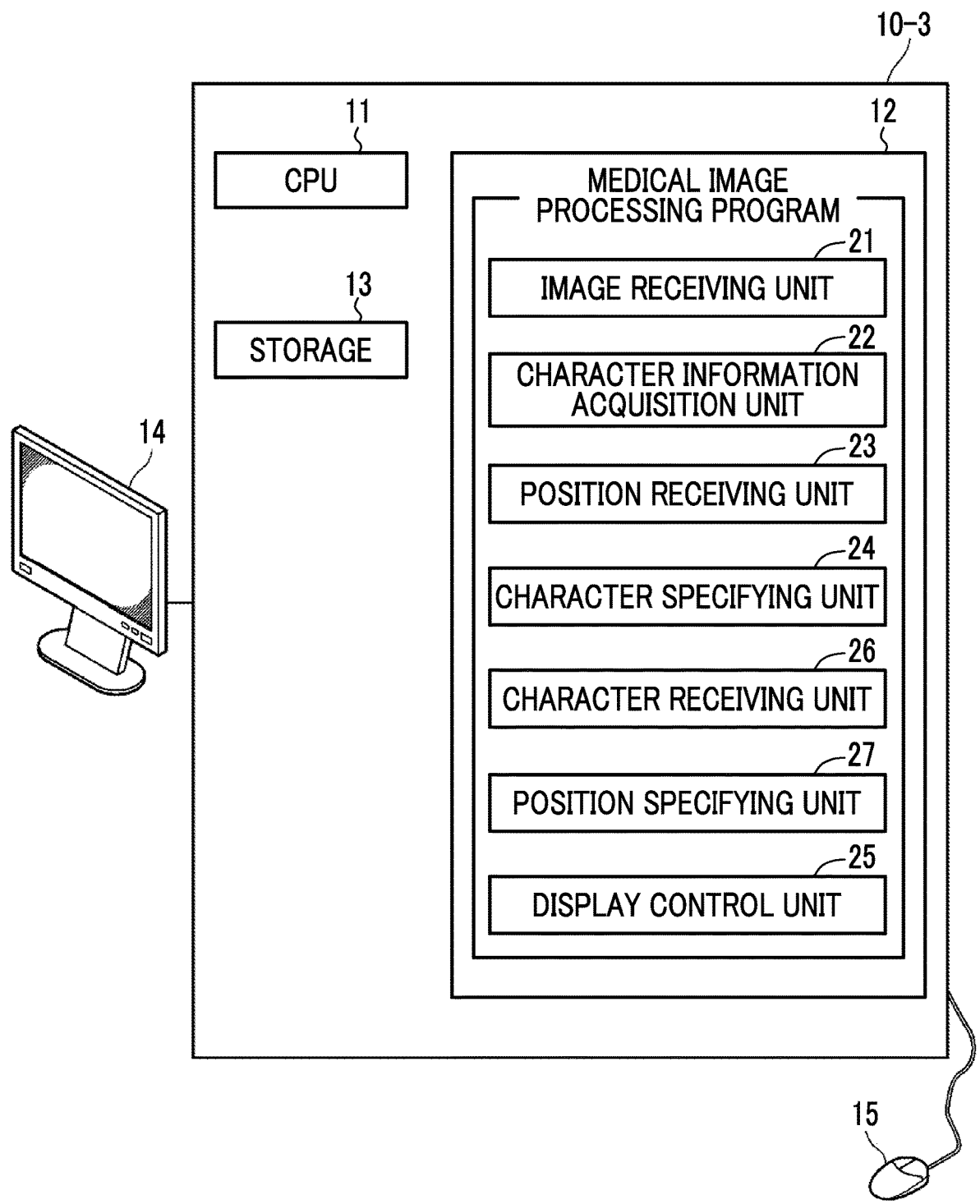
FIG. 15 is a diagram showing the schematic configuration of a medical image processing apparatus according to a third embodiment.

Next, an interpretation WS 3 according to a third embodiment will be described in detail. The interpretation WS 3 according to the third embodiment includes a medical image processing apparatus 10-3 according to the third embodiment. FIG. 15 is a diagram showing the schematic configuration of the medical image processing apparatus 10-3 according to the third embodiment. In FIG. 15, the same components as those in the first and second embodiments described above are denoted by the same reference numerals, and the description thereof will be omitted herein and only different components will be described in detail.

The medical image processing apparatus 10-3 shown in FIG. 15 further includes the character receiving unit 26 and the position specifying unit 27 in the configuration of the medical image processing apparatus 10 shown in FIG. 2.

Next, medical image processing performed in the third embodiment will be described. In the third embodiment, as an example, medical image processing at the time of creating an interpretation report for a CT image acquired for one subject will be described. It is assumed that the interpretation report created herein is a current interpretation report (hereinafter, referred to as a current report). FIG. 16 is a flowchart showing the medical image processing performed in the third embodiment.

Since the processing from step S21 to step S25 in FIG. 16 is the same processing as the processing from step S1 to step S5 in FIG. 3 of the first embodiment described above, the description thereof will be omitted herein.

In step S26, the position receiving unit 23 determines whether or not there is a designation of a position. In a case where there is a designation of a position by the radiologist in step S26 (step S26; YES), the position receiving unit 23 receives the designation of the position by the radiologist and acquires the coordinate position of the region of the cursor 39, that is, in the circle on the current image. Then, the CPU 11 proceeds to step S27.

Then, in step S27, in the same manner as in the processing of step S7 in FIG. 3, the character specifying unit 24 specifies characters relevant to the position received by the position receiving unit 23 from the character information acquired by the character information acquisition unit 22. Then, the character specifying unit 24 further searches for characters relevant to "part b" in the character information acquired by the character information acquisition unit 22. As an example, as shown in FIG. 5, the character string 40 of "There is B at part b." in the past interpretation report on Nov. 27, 2017 is specified as characters relevant to the position received by the position receiving unit 23, that is, the part b.

Then, in step S28, in the same manner as in the processing of step S8 in FIG. 3, the display control unit 25 performs control to display the character string 40 of "There is B at part b." specified by the character specifying unit 24 so as to be emphasized on the display unit 14. On the other hand, in a case where there is no designation of a position by the radiologist in step S26 (step S26; NO), the CPU 11 proceeds to step S29.

Then, in step S29, the character receiving unit 26 determines whether or not there is a designation of a character. In a case where there is a designation of a character by the radiologist in step S29 (step S29; YES), the character receiving unit 26 receives the designation of the character by the radiologist.

Then, in step S30, in the same manner as in the processing of step S17 in FIG. 12, the position specifying unit 27 specifies a position relevant to the characters received by the character receiving unit 26, that is, the character string 40 of "There is B at part b.", in the current image 35 received by the image receiving unit 21.

Then, in step S31, in the same manner as in the processing of step S18 in FIG. 12, the display control unit 25 performs control to display the region, which is indicated by the coordinate position on the current image 35 of the lesion B located at the part b specified by the position specifying unit 27, so as to be emphasized on the display unit 14.

On the other hand, in a case where there is no designation of a character by the radiologist in step S29 (step S29; NO), the CPU 11 proceeds to step S32.

Then, in step S32, the CPU 11 determines whether or not there is an end instruction in the interpretation WS 3. In a case where there is no end instruction (step S32; NO), the CPU 11 proceeds to step S26 to continue the process from step S26. In a case where there is an end instruction (step S32; YES), the CPU 11 ends the process.

As described above, in the third embodiment, in a case where the radiologist designates the part b by operating the cursor 39 in the current image 35, the character string 40 of "There is B at part b." is displayed as characters relevant to the part b so as to be emphasized in the character information of the past interpretation report. Therefore, the radiologist can easily visually recognize the characters displayed so as to be emphasized, that is, the character string 40 of "There is B at part b.", on the display unit 14. As a result, since the radiologist can easily check the contents of the findings in the past interpretation report for the part b, the interpretation efficiency is improved. In addition, at the time of creating the current interpretation report, the radiologist can create the findings with reference to the past finding contents for the part b.

In the third embodiment, in a case where the radiologist designates the character string 40 of "There is B at part b." as characters by operating the cursor 39 in the character information of the past interpretation report, the region of the lesion B of the part b is displayed as a position relevant to the character string 40 of "There is B at part b." so as to be emphasized in the current image 35. Therefore, the radiologist can easily visually recognize the position displayed so as to be emphasized, that is, the region of the lesion B of the part b, on the display unit 14. As a result, since the radiologist can easily check how "There is B at part b.", which is the finding contents of the past interpretation report, has progressed in the current image, the interpretation efficiency is improved. As described above, since the current image and the character information of the past interpretation report can be referred to, the interpretation efficiency is improved.

In the first to third embodiments described above, the current image is a tomographic image forming a three-dimensional image that is a CT image. However, the invention is not limited thereto. The three-dimensional image may be an MRI image, and the current image may be a tomographic image forming a three-dimensional image that is an MRI image.

In the first to third embodiments described above, the character information is acquired from the interpretation report. However, the character information may be acquired from a medical document other than an interpretation report, such as an electronic medical record and a diagnosis report.

EXPLANATION OF REFERENCES

1: medical information system
2: modality
3: interpretation workstation
4: medical department workstation
5: image server
6: image database
7: interpretation report server
8: interpretation report database
9: network
10, 10-2, 10-3: medical image processing apparatus
11: CPU
12: memory
13: storage
14: display unit
15: input unit
21: image receiving unit
22: character information acquisition unit
23: position receiving unit
24: character specifying unit
25: display control unit
26: character receiving unit
27: position specifying unit
30: interpretation report creation screen
31: patient information region
32: order information region
33: examination list region
34, 35: current image
36: creation region
37: past interpretation report region
37a: past interpretation report region
37b: past interpretation report region
37c: past interpretation report region
38: past image region
39: cursor
39A, 39B, 39C: round frame
40: character string
41: character string
42: character string
43: character

What is claimed is:

1. A medical image processing apparatus, comprising:
an image receiving unit that receives a current image acquired by imaging a subject;
a character information acquisition unit that acquires character information from past medical information relevant to the current image;
a position receiving unit that receives a designation of a position in the current image received by the image receiving unit;
a character specifying unit that specifies a character relevant to the position received by the position receiving unit from the character information acquired by the character information acquisition unit; and
a display control unit that performs control to display the character specified by the character specifying unit so as to be emphasized on a display unit;
wherein, in a case where a plurality of the characters are specified by the character specifying unit, the display control unit performs control to display the characters so as to be emphasized by weighting according to contents of the characters,
wherein, in a case where the character specifying unit does not specify a character relevant to the position received by the position receiving unit in the character information acquired from first past medical information and specifies the character in the character information acquired from second past medical information before the first past medical information, the display control unit performs control to display the character, which is specified in the second past character information by the character specifying unit, so as to be emphasized on the display unit and controls a notification unit to notify that the character has not been specified in the first past medical information.

2. The medical image processing apparatus according to claim 1,
wherein, in a case where the character information acquisition unit acquires the character information in a plurality of pieces of the past medical information, the display control unit performs control to display the character information for each of different pieces of the past medical information in a display method based on any one of parallel display, individual display, or overlapping display.

3. The medical image processing apparatus according to claim 1,
wherein the character includes feature information indicating a feature of a lesion.

4. A medical image processing apparatus, comprising:
an image receiving unit that receives a current image acquired by imaging a subject;
a character information acquisition unit that acquires character information from past medical information relevant to the current image;
a position receiving unit that receives a designation of a position in the current image received by the image receiving unit;
a character receiving unit that receives a designation of a character in the character information acquired by the character information acquisition unit;
a character specifying unit that specifies a character relevant to the position received by the position receiving unit from the character information acquired by the character information acquisition unit in a case where the designation of the position is received by the position receiving unit;
a position specifying unit that specifies a position relevant to the character received by the character receiving unit in the current image received by the image receiving unit in a case where the designation of the character is received by the character receiving unit; and
a display control unit that performs control to display the specified character so as to be emphasized on a display unit in a case where the character is specified by the character specifying unit and performs control to display the specified position so as to be emphasized on the display unit in a case where the position is specified by the position specifying unit;
wherein, in a case where a plurality of the characters are specified by the character specifying unit, the display control unit performs control to display the characters so as to be emphasized by weighting according to contents of the characters, and
wherein, in a case where a plurality of the positions are specified by the position specifying unit, the display control unit performs control to display the positions so as to be emphasized by weighting according to the positions,
wherein, in a case where the character specifying unit does not specify a character relevant to the position received by the position receiving unit in the character information acquired from first past medical information and specifies the character in the character information acquired from second past medical information before the first past medical information, the display control unit performs control to display the character, which is specified in the second past character information by the character specifying unit, so as to be emphasized on the display unit and controls a notification unit to notify that the character has not been specified in the first past medical information.

5. The medical image processing apparatus according to claim 4,
wherein, in a case where the character information acquisition unit acquires the character information in a plurality of pieces of the past medical information, the display control unit performs control to display the character information for each of different pieces of the past medical information in a display method based on any one of parallel display, individual display, or overlapping display.

6. The medical image processing apparatus according to claim 4, wherein:
in a case where a plurality of the positions are specified by the position specifying unit, the display control unit performs control to display the positions so as to be emphasized in the current image by weighting according to the positions.

7. A medical image processing method, comprising:
a processor configured to perform the steps of;
receiving a current image acquired by imaging a subject;
acquiring character information from past medical information relevant to the current image;
receiving a designation of a position in the received current image;
specifying a character relevant to the received position from the acquired character information;
performing control to display the specified character so as to be emphasized on a display unit; and
performing, in a case where a plurality of the characters are specified, control to display the characters so as to be emphasized by weighting according to contents of the characters,
in a case where the character relevant to the received position is not specified in the character information acquired from first past medical information and is specified in the character information acquired from second past medical information before the first past medical information, performing control to display the character, which is specified in the second past character information, so as to be emphasized on the display unit and control to notify that the character has not been specified in the first past medical information.

8. A medical image processing method, comprising:
a processor configured to perform the steps of;
receiving a current image acquired by imaging a subject;
acquiring character information from past medical information relevant to the current image;
receiving a designation of a position in the received current image or receiving a designation of a character in the acquired character information;
specifying a character relevant to the received position from the acquired character information in a case where the designation of the position is received and performing control to display the specified character so as to be emphasized on a display unit;
specifying a position relevant to the received character in the received current image in a case where the designation of the character is received and performing control to display the specified position so as to be emphasized on the display unit;
performing, in a case where a plurality of the characters are specified, control to display the characters so as to be emphasized by weighting according to contents of the characters; and
performing, in a case where a plurality of the positions are specified, control to display the positions so as to be emphasized by weighting according to the positions
in a case where the character relevant to the received position is not specified in the character information acquired from first past medical information and is specified in the character information acquired from second past medical information before the first past medical information, performing control to display the character, which is specified in the second past character information, so as to be emphasized on the display unit and control to notify that the character has not been specified in the first past medical information.

9. A non-transitory computer-readable recording medium causing a computer to execute:
a step of receiving a current image acquired by imaging a subject;

a step of acquiring character information from past medical information relevant to the current image;

a step of receiving a designation of a position in the received current image;

a step of specifying a character relevant to the received position from the acquired character information;

a step of performing control to display the specified character so as to be emphasized on a display unit; and a step of performing, in a case where a plurality of the characters are specified, control to display the characters so as to be emphasized by weighting according to contents of the characters, wherein, in a case where the character relevant to the received position is not specified in the character information acquired from first past medical information and is specified in the character information acquired from second past medical information before the first past medical information, causing the computer to further execute a step of performing control to display the character, which is specified in the second past character information, so as to be emphasized on the display unit and control to notify that the character has not been specified in the first past medical information.

10. A non-transitory computer-readable recording medium causing a computer to execute:

a step of receiving a current image acquired by imaging a subject;

a step of acquiring character information from past medical information relevant to the current image;

a step of receiving a designation of a position in the received current image or receiving a designation of a character in the acquired character information;

a step of specifying a character relevant to the received position from the acquired character information in a case where the designation of the position is received and performing control to display the specified character so as to be emphasized on a display unit;

a step of specifying a position relevant to the received character in the received current image in a case where the designation of the character is received and performing control to display the specified position so as to be emphasized on the display unit;

a step of performing, in a case where a plurality of the characters are specified, control to display the characters so as to be emphasized by weighting according to contents of the characters; and a step of performing, in a case where a plurality of the positions are specified, control to display the positions so as to be emphasized by weighting according to the positions, wherein, in a case where the character relevant to the received position is not specified in the character information acquired from first past medical information and is specified in the character information acquired from second past medical information before the first past medical information, causing the computer to further execute a step of performing control to display the character, which is specified in the second past character information, so as to be emphasized on the display unit and control to notify that the character has not been specified in the first past medical information.

* * * * *